United States Patent [19]

Eyler

[11] Patent Number: 4,542,641

[45] Date of Patent: Sep. 24, 1985

[54] METHOD AND MEANS FOR THE DETECTION OF CHEMICAL AGENT DROPLETS

[76] Inventor: Roger C. Eyler, 7501A Ridge Rd., Frederick, Md. 21701

[21] Appl. No.: 558,894

[22] Filed: Dec. 7, 1983

[51] Int. Cl.⁴ .............................................. G01N 1/22
[52] U.S. Cl. ......................................... 73/26; 73/29; 73/159; 73/863.12
[58] Field of Search .................. 73/25, 26, 28, 29, 53, 73/61.3, 159, 862.11, 863.12, 864.21, 864.72

[56] References Cited

U.S. PATENT DOCUMENTS

| | | | |
|---|---|---|---|
| 2,890,797 | 6/1959 | Matthews | 73/61 R X |
| 3,011,336 | 12/1961 | Weiss | 73/29 |
| 3,400,575 | 9/1968 | Madden | 73/61 R |
| 3,705,021 | 12/1972 | Sundberg et al. | 210/497.1 X |
| 4,178,794 | 12/1979 | Jugle et al. | 73/28 |
| 4,223,552 | 9/1980 | Goldstein | 73/61.1 R |
| 4,257,257 | 3/1981 | Dairaku et al. | 73/19 |
| 4,350,507 | 9/1982 | Greenough et al. | 73/28 X |
| 4,391,338 | 7/1983 | Patashnick et al. | 73/28 X |

Primary Examiner—Robert Spitzer
Attorney, Agent, or Firm—Roland H. Shubert

[57] ABSTRACT

Falling liquid droplets of a chemical agent are detected by providing a droplet collector assembly which includes an air permeable surface member disposed to intercept falling droplets and adapted to cause vaporization of the intercepted droplets into a sample air stream drawn through the surface member. The sample air stream containing droplet vapor is then led into the sample inlet of a vapor detector.

30 Claims, 9 Drawing Figures

METHOD AND MEANS FOR THE DETECTION OF CHEMICAL AGENT DROPLETS

BACKGROUND OF THE INVENTION

This invention relates generally to a device for the detection of droplets of a chemical agent.

More specifically, this invention relates to a device for the detection of chemically active liquid droplets falling upon a surface and to a method for its use.

The chemical warfare capabilities of potential adversary nations is well documented. This potential threat comprises a broad array of chemical weapons including artillery, multiple rocket launchers, missiles, bombs and spray tank type chemical agent delivery systems. In fact, some of these chemical weapons have been used in localized foreign conflicts.

A wide variety of chemical agents are known to be in the arsenals of other nations. The principal threat agent is considered to be the nerve agent Soman, commonly referred to as GD. Soman and similar nerve agents such as Sarin and Tabun are commonly referred to as nerve gases but this is something of a misnomer. All are liquids with a relatively high boiling point and a relatively low vapor pressure. Soman, for example, has a normal boiling point of 167° C.

Munitions designed to deliver nerve and other chemical agents typically produce a rain of liquid droplets which fall to the ground. Size of the droplets formed by the various delivery systems varies greatly. Artillery and small rocket munitions produce droplet clouds with droplet mass median diameters of about 150 microns. Aircraft sprays typically produce droplets of about that same size. Chemical agents delivered by bombs may have a mass median droplet diameter of 1000 to 1,500 microns and missiles may deliver even larger droplets; up to 3,000 microns. As can be appreciated, a detector having the capability of providing the earliest possible warning must respond to a very broad range of droplet sizes; from about 50 to 5,000 microns.

Chemical warfare agents such as the nerve agents produce casualities in several ways. If troops are in the fall out area as the droplets rain to the ground, then direct contact with the agent occurs resulting in casualties from percutaneous absorption of the liquid agent. Troops entering a contaminated area also are exposed to direct contact with the liquid agent again resulting in percutaneous absorption. As the agent evaporates a vapor hazard is created which may result in casualties by inhalation. It is of utmost concern that detection and warning of a chemical agent attack be as early as possible. That requires the capability of detecting the fall of agent droplets as well as detecting the presence of vapor in an area.

Currently, there are only two automatic detection and alarm devices available to our troops in the field. One, the M8-E1 alarm is used by the Army and Marines. The other, the IDS alarm, is used by the Air Force and Navy. Neither of these alarms can detect droplets having a mass median diameter above about 50 microns as both draw in an air sample and require that the agent be in vapor form for detection.

Several improved detector and alarm systems are presently under development. Only one of these, the Automatic Liquid Agent Detector System (ALADS), will have a droplet detection capability. The ALADS detector relies upon the impaction of droplets upon a detector plate comprising a conducting circuit whose characteristics are changed as the agent droplet dissolves a conducting matrix. This detector is sensitive only to droplets having a diameter greater than about 200 microns.

There are important civilian, as well as military, needs for a device having the capability of detecting the fall of chemically active agents. Among the most important of these civilian needs is the monitoring of agricultural pesticide and herbicide spray applications. Civilian applications of such detecting devices can in some instances, as for example the application of certain pesticides, use the same detection system as do the military devices.

Although there has been a long recognized need for a device capable of detecting the fall of chemically active liquid droplets, no practical system for so doing has yet been devised. Ideally, such a system would have the capability of detecting both droplets and vapor; would operate dependably over a large temperature range; would be simple in construction and would be dependable in operation.

SUMMARY OF THE INVENTION

Liquid droplets of a chemical agent are detected by providing a droplet collector means disposed to intercept the droplets. The collector means are provided with a droplet interception surface which is permeable to air and which is adapted to enhance the vaporization of liquid into a sample air stream drawn through the surface. The sample stream is passed from the collector means to a detector which reacts to the presence of chemical agent vapor. The device is particularly applicable to the early detection of chemical warfare agents, especially the nerve agents, and to the monitoring of aerial spray application and drift of agricultural pesticides and herbicides.

Hence, it is an object of this invention to detect falling liquid droplets of a chemical agent.

It is another object of this invention to provide a method and means for the early detection of chemical agent use.

A specific object of this invention is to provide early warning of chemical agent attack.

Another specific object of this invention is to monitor the application of aerially applied agricultural chemicals and to detect the extent of spray drift.

Other objects of this invention will be apparent from the following description of certain embodiments of the invention.

BRIEF DESCRIPTION OF THE DRAWING

The invention is illustrated by the following drawing figures wherein the same numerals refer to the same parts and in which.

DESCRIPTION AND DISCUSSION OF THE INVENTION

Figure 2:
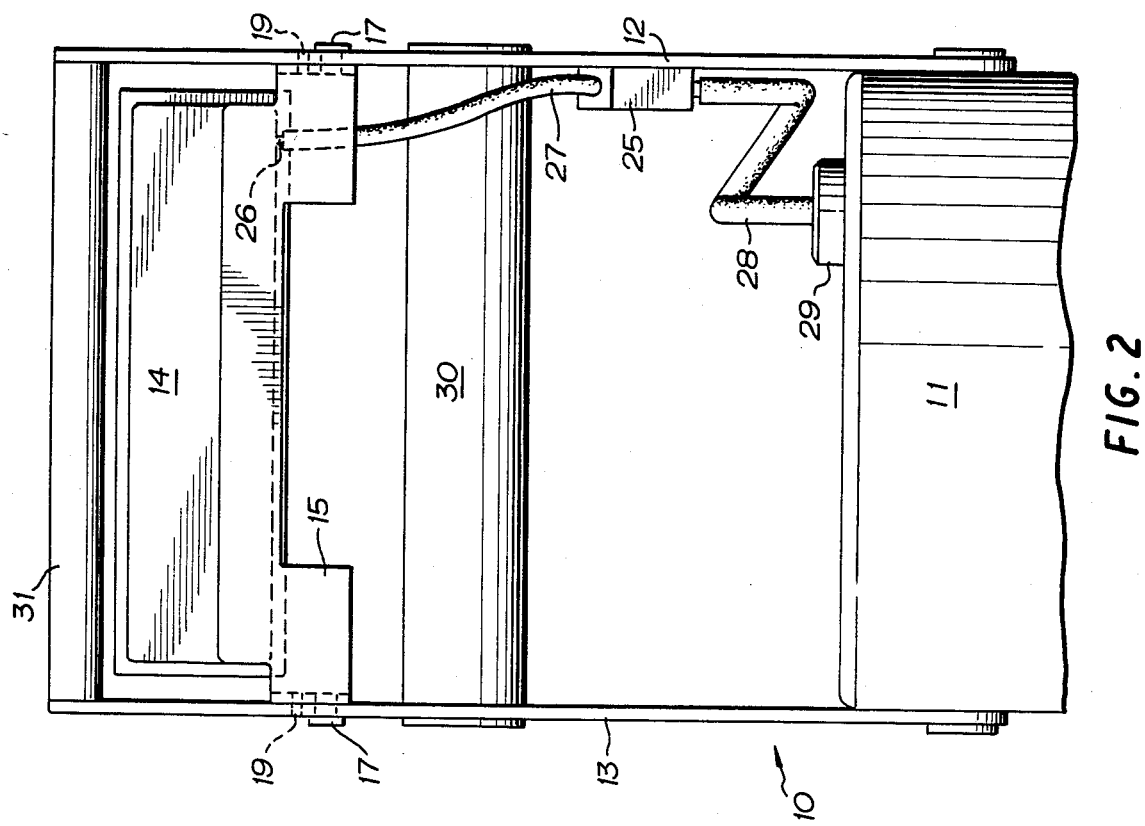
FIG. 2 is a front elevational view thereof.

The invention will be described with reference to the drawing in which a chemical agent detection device adapted to respond to liquid droplets is shown at 10 of FIG. 1 and is shown in another view in FIG. 2. Device 10 includes a chemical agent detector 11 which responds to small concentrations of chemical agent vapor carried through the detector in a sampled air stream. Detectors of this sort are well known and may comprise an ionization cell utilizing a radioactive source. Detector 11 is ordinarily arranged to produce an audio or visual signal or alarm upon responding to a chemical agent.

In one preferred embodiment a droplet collector assembly is mounted upon and disposed above a conventional chemical agent detector unit such as, for example, the military M8-A1 unit. This embodiment, generally illustrated in FIGS. 1 and 2, utilizes a pair of brackets, 12 and 13, attached to the sides of the detector case and extending above the case top to support the collector assembly. The collector assembly comprises one or more droplet collector means 14. Each of the droplet collector means 14 is mounted upon support means 15 and 16 which are pivotally attached to the brackets at 17 and 18 respectively. Pin 19 is fixed to and extends outwardly from support means 15 within arcuate guideway 20 to limit the travel of collector means 14 between a horizontal and vertical position. Likewise, pin 21 traveling within guideway 22 similarly limits the movement of the other of collector means 14.

Conduit means 23 communicates with the interior of one of collector means 14 and is connected to flexible tubing 24 leading to manifold 25. Likewise, conduit 26 communicates with the interior of the other of collector means 14 with tubing 27 connecting the conduit to manifold 25. Gases drawn from collector means 14 through tubing means 24 and 27 are merged within manifold 25 and thence are passed by way of tubing 28 to the sample inlet 29 of detector unit 11. Tubing means 24, 27 and 28 are preferably fabricated of an inert, flexible plastic such as Teflon.

A tubular carrying handle 30 is conveniently provided to extend between bracket members 12 and 13 at a location below collector means 14. There may also be provided a rod or bar 31 extending between the bracket members at the top thereof to provide protection for the collector means 14. Collector means 14 are disposed in a generally horizontal attitude, as shown in FIG. 1, while detector unit 11 is in operation and are rotated to a generally vertical attitude, as shown in FIG. 2, for carrying or storage.

Figure 3:
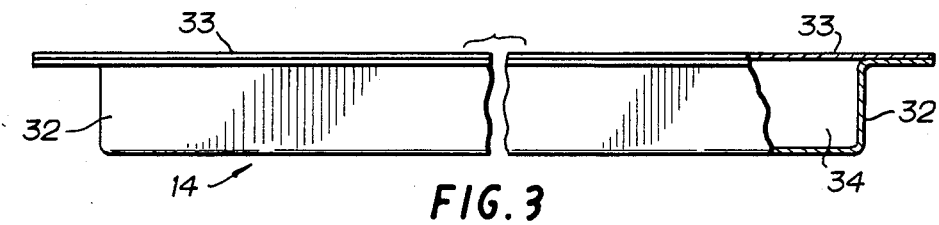
FIG. 3 is a side view in partial section of the collecting means and chamber.
Figure 4:
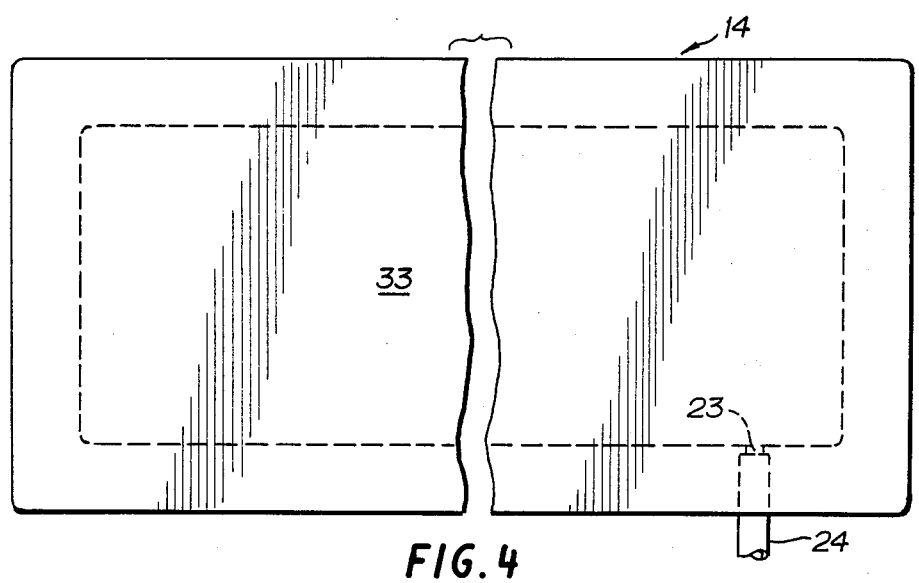
FIG. 4 is a top plan view of the collecting means and chamber of FIG. 3.

Turning now to FIGS. 3 and 4, there is shown collector means 14 in greater detail. Means 14 comprises generally a housing 32 disposed about the lower surface of a droplet interception and vaporization sheet member 33 to form a chamber 34. As shown in FIG. 4, there is provided a conduit means 23 communicating between chamber 34 and the exterior thereof and connectable to tubing 24.

Sheet member 33 functions both to intercept a falling liquid droplet and to facilitate its vaporization. In order to accomplish this result, sheet member 33 must have certain characteristics. It must be permeable to air as the air sample drawn through the detector unit must first pass through member 33. It must be of relatively uniform permeability and porosity so that air does not preferentially channel through one portion of the member. It also must cause an increase, preferably a very substantial increase, in the evaporation rate of a liquid droplet after impact on the sheet member. Increasing the droplet evaporation rate may be accomplished in several ways. Sheet member 33 may be heated or otherwise held at a temperature above ambient. The member may induce a rapid catalytic or chemical action to transform the liquid droplet of chemical agent into a more volatile species. Member 33 may be of such material and construction as to vastly increase the liquid surface area exposed to the air stream thereby causing a greatly accelerated evaporation rate.

Figure 5:
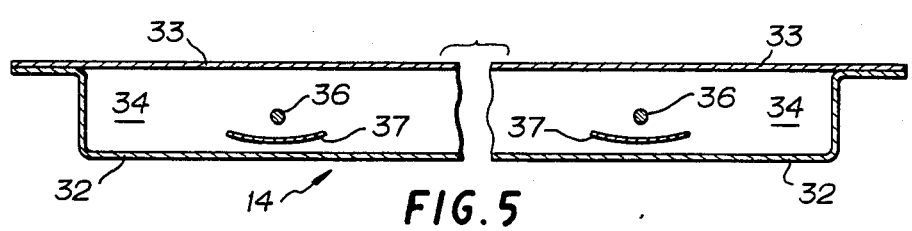
FIG. 5 is a sectional view of the collecting means and chamber of FIG. 3 with heater means.

Heating sheet member 33 may be accomplished in several ways, one preferred approach being illustrated in FIG. 5. As shown in that Figure, one or more heated filaments or ribbons 36 are disposed within chamber 34 of collector means 14. Filaments 36 may conveniently comprise resistance wire through which an electric current is passed. Radiant energy is thus directed upon the lower surface of sheet means 33. Heating efficiency may be increased by the provision of reflectors 37 shaped to direct radiation onto the surface of sheet 33. If member 33 is fabricated of an electrically conductive material, it also may be heated by passing an electric current through the sheet member itself.

Sheet member 33 may be fabricated to include chemical reactants or catalytic materials which act to convert a chemical agent to a more volatile form or species. For example, a porous, filter-like sheet incorporating a mixture of silver nitrate and potassium fluoride will act to convert V-type nerve agents to Sarin (GB) which is considerably more volatile. A conversion filter of this type may be constructed by impregnating a woven or felted fabric with a solution of the reactant chemicals and thereafter drying to leave the chemicals associated throughout the filter.

In a generally preferred embodiments, sheet member 33 comprises a filter-like membrane wettable by the liquid chemical agent to be detected. A liquid droplet impacting upon a membrane of this sort spreads rapidly across and through the membrane increasing the liquid surface area exposed to the sample air stream by many orders of magnitude. The liquid rapidly evaporates passing as vapor into the sample air stream and thence through the detector.

It has been found that a randomly oriented, stainless steel fibril mat of the type used for filtration of oils and the like performs very well in this application. Such metal fibril mats are fabricated by air laying metal fibrils to form a loose mat; compressing the mat and annealing it; and thereafter further compressing the mat and sintering it to form bonds between contacting fibrils in the manner described, for example, in U.S. Pat. No. 3,705,021. Metal fibril mats of this sort are a commercial product manufactured by the Brunswick Corporation.

It has been found that stainless steel fibril mats are readily wet by liquid chemical agents such as the nerve agents and similar chemical compounds. A liquid droplet impacting upon the mat rapidly spreads across and through the mat to provide a vastly increased liquid surface area causing rapid evaporation of the liquid into the sample air stream passing through the mat. Mat thickness suitably may range from about 0.01 to about 0.02 inches with an appropriate pore size being on the order of 20 microns.

Other materials, such as closely woven screen or fabric also may find use as sheet member 33. The screen or fabric may be constructed of metal or of non-metallic fibers. In all cases, it is important that the pore size or screen opening be smaller than about 50 microns so that droplets cannot pass through member 33 but are intercepted by the sheet member and are caused to spread thereon.

Figure 1:
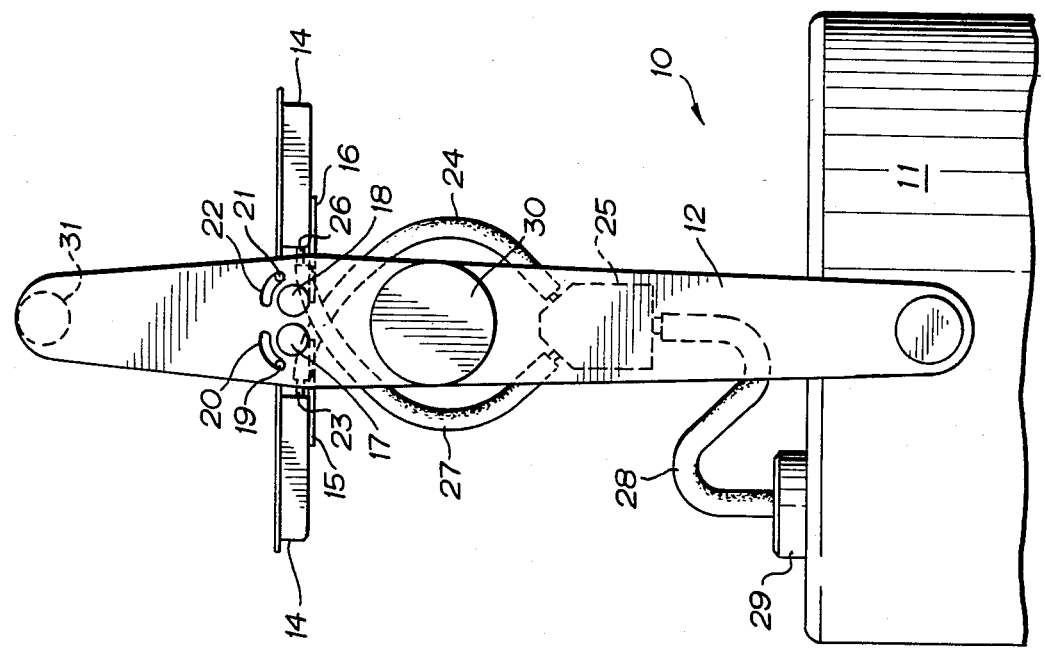
FIG. 1 is a side elevation view of a device for detecting liquid droplets of a chemical agent in accordance with this invention.

In a preferred embodiment of this invention, described in relation to FIGS. 1 and 2, collector means 14 was shown disposed in a stationary attitude above a detector unit 11. It is necessary for the proper functioning of collector 14 that it be positioned at a location which does not obstruct the fall of liquid droplets onto sheet member 33. Hence, under most conditions, collector means 14 could equally well be placed to the side of, rather than on top of, the detector unit. Further, provision can be made to automatically orient collector means 14 to the most favorable position for intercepting falling droplets.

Figure 6:
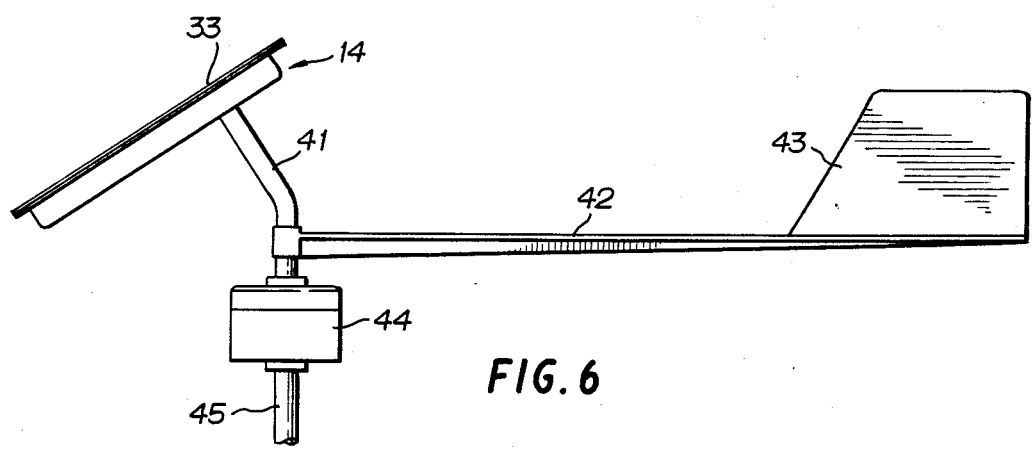
FIG. 6 depicts another embodiment of the collecting means and chamber.

FIG. 6 depicts another embodiment of this invention wherein collector unit 14 is arranged to automatically point into the wind. In this embodiment, collector unit 14 and sheet member 33 are canted at an angle, suitably about 35° to 40°, to the horizontal. Collector 14 is mounted upon a tubular support 41 attached to a boom 42 having a wind vane 43 at its far end. The entire assembly is freely rotatable about a low-friction bearing mount 44. Conduit means are provided within support 41 from the interior chamber of collector 14 through bearing mount 44 and lead via tubing 45 to the sample inlet port of a detector unit. This configuration increases the droplet collection efficiency of the unit under windy conditions and can be employed with standard detectors in place of the stationary collector array depicted in FIGS. 1 and 2.

Figure 7:
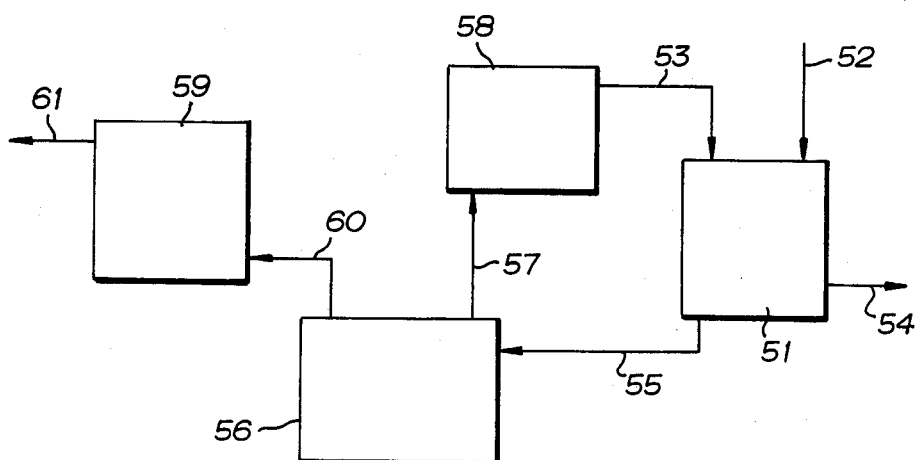
FIG. 7 is a schematic diagram of detection means suitable for use with the collecting means and chamber of FIGS. 3 to 6.

Suitable means for the detection of chemical agents are shown schematically in FIG. 7. The detection means comprises a detector cell 51 which conveniently may be an ionization detector employing a radioactive source. A gas sample, typically air, is introduced into cell 51 via sample inlet 52 wherein it is mixed and reacted with liquid reagent stream 53. Reagent 53 may be a caustic solution which is reactive toward chemical agent vapor carried in sample stream 52 to produce ionic species detectable by cell 51. In response to the presence of ions, cell 51 produces an electronic signal 54 which in turn activates an alarm or display (not shown).

A combined stream of sample gas and liquid reagent 55 is circulated from the cell to a separator and reagent reservoir unit 56. Liquid reagent separated from the sample gas is pumped from reservoir 56 through tubing 57 by means of pump 58 and returned again to cell 51. An air pump 59 draws the sample stream from reservoir 56 by way of conduit 60 and discharges it from the system at 61.

In practical application, such as in the monitoring of pesticide or herbicide spray drift or to provide immediate warning of chemical agent attack, detector units having liquid droplet collection means are placed in suitable monitoring locations. An air sample is continuously drawn through the droplet collection means and thence through the detector unit at an air flow rate typically on the order of about one liter per minute. The detector will respond to the presence of chemical agent vapor, whether that vapor is generally present in the air mass or was derived from a liquid droplet striking the droplet collector means, and will trigger an alarm or otherwise note the event.

In order to be of greatest value when employed to warn of chemical agent attack, the device of this invention necessarily must respond to levels of chemical agent below, and preferably far below, those levels which produce a significant military threat. The standard vapor detector currently employed is sensitive to extemely low levels of chemical agent vapor. However, because of the low volatility of the nerve agents, a detector which responds only to vapor experiences an alarm delay of significant scope. That alarm delay time is dependent upon the type of nerve agent employed, VX has a much lower vapor pressure than GD; upon the ambient temperature as volatility is of course a function of temperature; upon the droplet size of the applied agent; and upon the level or concentration of agent applied in proximity to the detector.

A series of calculations were performed to determine the theoretical response characteristics of the standard military M8-A1 vapor detector unit equipped with the liquid droplet detection device of this invention. These calculations were based upon a droplet collection area of 16 square inches and assumed well ventilated spherical droplets of nerve agent to determine evaporation rates. A summary of the calculations is presented in the following table.

TABLE 1

| Temp. (°C.) | Agent | Droplet Diameter (microns) | Drops to Trigger Alarm | Drops/m$^2$ | Drops/m$^2$ To Threat | Alarm Safety Factor |
|---|---|---|---|---|---|---|
| 4 | VX | 100 | $1.10 \times 10^3$ | $1.07 \times 10^5$ | $1.91 \times 10^6$ | 17.8 |
|   |    | 200 | $5.16 \times 10^2$ | $5.00 \times 10^4$ | $2.39 \times 10^5$ | 4.8 |
|   |    | 400 | $2.39 \times 10^2$ | $2.31 \times 10^4$ | $2.98 \times 10^4$ | 1.3 |
|   |    | 800 | $1.22 \times 10^2$ | $1.19 \cdot 10^4$ | $3.73 \times 10^3$ | .31 |
|   |    | 1600 | $5.60 \times 10$ | $5.42 \times 10^3$ | $4.66 \times 10^2$ | $8.60 \times 10^{-2}$ |
|   |    | 3200 | $2.75 \times 10$ | $2.67 \times 10^3$ | $5.83 \times 10$ | $2.18 \times 10^{-2}$ |
| 4 | GD | 100 | 3.82 | $3.70 \times 10^2$ | $3.82 \times 10^6$ | $1.03 \times 10^4$ |
|   |    | 200 | 1.80 | $1.74 \times 10^2$ | $4.77 \times 10^5$ | $2.74 \times 10^3$ |
|   |    | 400 | $8.59 \times 10^{-1}$ | $8.33 \times 10$ | $5.97 \times 10^4$ | $7.16 \times 10^2$ |
|   |    | 800 | $6.27 \times 10^{-1}$ | $6.07 \times 10$ | $7.46 \times 10^3$ | $1.23 \times 10^2$ |
|   |    | 1600 | $1.90 \times 10^{-1}$ | $1.84 \times 10$ | $9.33 \times 10^2$ | $5.07 \times 10$ |
|   |    | 3200 | $8.86 \times 10^{-2}$ | 8.58 | $1.17 \times 10^2$ | $1.36 \times 10$ |
| 18 | VX | 100 | $3.21 \times 10^2$ | $3.11 \times 10^4$ | $1.91 \times 10^6$ | 61.4 |
|    |    | 200 | $1.55 \times 10^2$ | $1.50 \times 10^4$ | $2.39 \times 10^5$ | 15.9 |
|    |    | 400 | $7.40 \times 10$ | $7.17 \times 10^3$ | $2.98 \times 10^4$ | 4.16 |

TABLE 1-continued

| Temp. (°C.) | Agent | Droplet Diameter (microns) | Drops to Trigger Alarm | Drops/m$^2$ | Drops/m$^2$ To Threat | Alarm Safety Factor |
|---|---|---|---|---|---|---|
|  |  | 800 | $5.97 \times 10$ | $5.78 \times 10^3$ | $3.73 \times 10^3$ | .65 |
|  |  | 1600 | $1.60 \times 10$ | $1.55 \times 10^3$ | $4.66 \times 10^2$ | .30 |
|  |  | 3200 | 7.46 | $9.69 \times 10$ | $5.83 \times 10$ | .60 |
| 18 | GD | 100 | 1.02 | $9.92 \times 10$ | $3.82 \times 10^6$ | $3.85 \times 10^4$ |
|  |  | 200 | $4.97 \times 10^{-1}$ | $4.81 \times 10$ | $4.77 \times 10^5$ | $9.93 \times 10^3$ |
|  |  | 400 | $2.36 \times 10^{-1}$ | $2.29 \times 10$ | $5.97 \times 10^4$ | $2.61 \times 10^3$ |
|  |  | 800 | $1.10 \times 10^{-1}$ | $1.07 \times 10$ | $7.46 \times 10^4$ | $6.97 \times 10^2$ |
|  |  | 1600 | $5.60 \times 10^{-2}$ | 5.42 | $9.33 \times 10^2$ | $1.72 \times 10^2$ |
|  |  | 3200 | $2.75 \times 10^{-2}$ | 2.67 | $1.17 \times 10^2$ | $4.37 \times 10$ |

As can be seen from the data in Table 1 a droplet collector having a collecting area of 16 in$^2$ will intercept a sufficient number of falling droplets to provide a significant alarm safety factor in the case of GD throughout the range of anticipated droplet diameters at temperatures as low as 4° C. An alarm safety factor of 1 represents that concentration of droplets producing a ground contamination level considered to be a militarily significant threat as is set out in published reports on nerve agents. In the case of GD, ground concentration densities of 1,920 mg/m$^2$ at 18° C. and 3,180 mg/m$^2$ at 4° C. are considered to be of military significance. Agent VX is of lower volatility than is GD. Consequently, the calculations indicated that alarm safety factors greater than unity would be provided for droplet sizes smaller than about 400 microns at both 4° and 18° C.

A liquid agent collection device conforming generally in structure to that depicted in FIGS. 1 and 2 was fabricated and mounted upon a military M8-A1 chemical agent vapor detection unit. The liquid droplet collection surface was 16 in$^2$ in area and sheet member 33 comprised a metal fibril filter membrane having a thickness of approximately 0.02 inches supplied by Brunswick Corporation. Air flow rate through the droplet collector means and through the detector was approximately 1 l/min. This unit was then tested and its performance evaluated using simulants rather than live nerve agents. The simulants used were diethyl-ethyl phosphonate (DEEP) and tripropylphosphate (TPF). These simulants were selected as they conform quite closely in volatility to the nerve agents, produce an essentially equivalent detector response as do the nerve agents, and are far far less toxic than are the nerve agents.

One group of experiments was performed in a test chamber using DEEP as the simulant. Temperature of the test chamber was controlled as was the air or wind, velocity across the collector-detector unit. In all cases, the surface of the droplet collector was innoculated with a single 0.5 microliter simulant drop having a calculated spherical diameter of about 985 microns. The time delay between innoculation and alarm was measured for each test and the following results were obtained:

TABLE 2

| Temperature (°C.) | Wind Speed (m/sec) | Time to Alarm (sec) |
|---|---|---|
| 21 | 3 | 8 |
| 8 | 3 | 12 |
| −7 | 3 | 116 |
| 21 | 8 | 15 |
| 7 | 8 | 23 |
| −7 | 8 | 132 |

Figure 8:
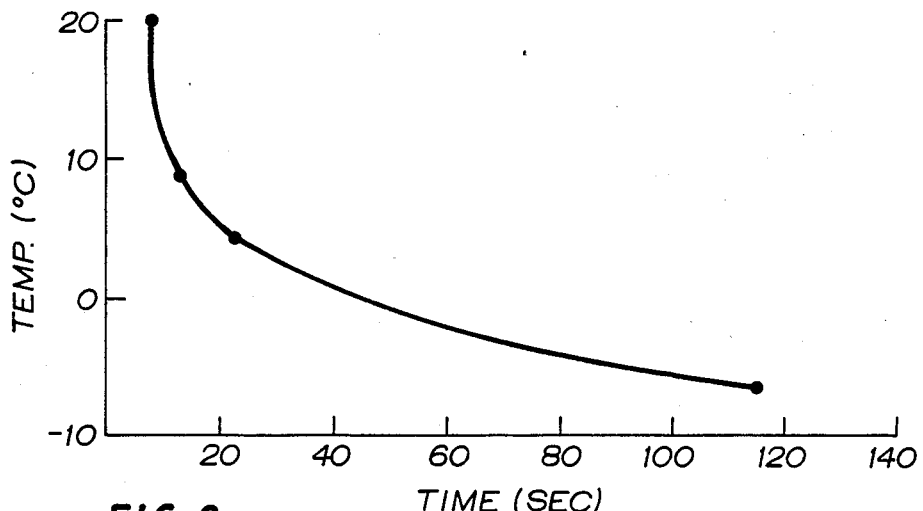
FIG. 8 is a plot of detector response time versus temperature displayed by an exemplary chemical agent liquid droplet detection device according to this invention.

Based upon these results along with additional tests, a plot of alarm response time versus temperature was derived using DEEP as a simulant. This plot is presented as FIG. 8.

Figure 9:
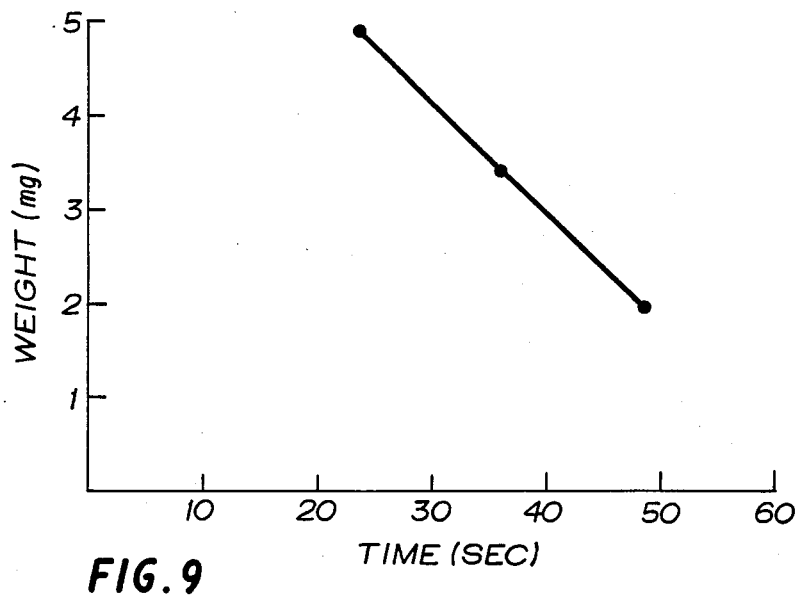
FIG. 9 is a plot of detector response time versus weight of a single liquid droplet at constant temperature.

A further series of experimental tests was performed using TPF as a simulant. The tests were run at a constant temperature of 90° F. (32° C.) to determine the relationship between droplet weight and alarm response time. In all cases, the surface of the droplet collector was innoculated with a single liquid droplet and the time delay between innoculation and alarm was measured. Results obtained are presented as FIG. 9. As can be seen from that plot, there is indicated a linear relationship between droplet weight and detector response time.

These experimental results were extrapolated to provide projected performance characteristics of the collector-detector unit with live nerve agents. The following results were obtained:

TABLE 3

| Agent | Temperature (°C.) | Droplet Size (microns) | Minimum Ground Contamination at Alarm (mg/m$^2$) |
|---|---|---|---|
| GD | 18 | 200 | 0.4 |
|  |  | 400 | 3.3 |
|  |  | 800 | 26.3 |
|  |  | 1600 | 208.8 |
|  |  | 3200 | 1678.0 |
| GD | 4 | 200 | 0.7 |
|  |  | 400 | 3.3 |
|  |  | 800 | 26.3 |
|  |  | 1600 | 208.8 |
|  |  | 3200 | 1678.0 |
| VX | 18 | 100 | 16.4 |
|  |  | 200 | 63.4 |
| VX | 4 | 100 | 55.8 |
|  |  | 200 | 209.0 |

It is significant to note here in relation to the minimum level of ground contamination expected at time of alarm in the larger droplet size ranges that the calculated results represent in effect a worst case analysis. For example, in the case of GD at a 200 micron droplet size at 18° C., a minimum ground contamination of 0.4 mg/m$^2$ is expected at time of alarm. Far less than 0.4 mg falling on the droplet collector surface will trigger that alarm. Detector sensitivity remains constant in terms of vapor concentration and is independent of droplet size. However, a far greater mass of chemical agent falling on any particular square meter will be required to statistically ensure interception of at least one droplet on the collector surface in the case of the larger droplets. As a practical matter, application of a chemical agent by whatever means results in a very broad range of liquid droplet diameters. Thus if the mean droplet diameter were 1600 microns, for example, there would also be a very significant population of much smaller droplets;

down to and including droplets of 100 microns or less in diameter. The larger number of smaller droplets would substantially increase the statistical likelihood of droplets being intercepted by the collector means and could be expected to trigger an alarm at ground contamination levels below those calculated.

As can be appreciated, the minimum ground contamination at time of alarm is a function of the surface area of the droplet collector. To a degree, increased sensitivity to liquid droplets can be obtained by increasing the area of the droplet collector. There are practical constraints to the advantages gained by increasing the collector area. While all theoretical calculations and practical tests were based upon a droplet collector area of 16 in$^2$, this collector area may be increased or decreased within rather broad limits. Generally speaking, a preferred collector surface area will range from about 5 to about 50 in$^2$ depending upon the sensitivity of the vapor detector used in association with the droplet collector and depending upon the needs of the particular application.

The vapor detector unit used in association with the liquid droplets collection device has been described as an ionization detector employing a radioactive source. Such detectors are extemely sensitive, light in weight and highly portable. However, other detector systems including those using infrared or ultraviolet spectral analysis may be used as well so long as that other system can be assembled as a rugged, sensitive and relatively compact field unit capable of unmonitored operation over extended periods of time.

Many other embodiments of and uses for this invention will be apparent to those skilled in the art without departing from the spirit and scope of the following claims.

I claim:

1. Means for adapting a chemical agent vapor detection and alarm device to respond to liquid droplets of a chemical agent, comprising:
a liquid droplet collector assembly mountable upon said detection and alarm device, said collector assembly having at least one droplet collector means adapted to be disposed in an attitude generally perpendicular to the path of falling droplets, said collector means including a sheet member permeable to air, said sheet member positioned at a location free from obstruction to said falling droplets and adapted to enhance the vaporization of liquid droplets falling thereupon;
housing means disposed about the lower side of said sheet member to form a chamber, and
conduit means communicating between the interior of said chamber and a sample inlet port of said detection and alarm device.

2. The means of claim 1 wherein said sheet member is of substantially uniform porosity and permeability over its entire area.

3. The means of claim 2 including heating means to adapted to maintain said sheet member at a temperature above ambient.

4. The means of claim 3 wherein said heating means include electrical resistance filaments disposed within said chamber and arranged to direct radiant energy onto said sheet member.

5. The means of claim 2 wherein said sheet member includes chemical reactants or catalytic materials adapted to convert said chemical agent to a more volatile species.

6. The means of claim 5 wherein said chemical reactants include silver nitrate and potassium fluoride and are adapted to convert V-type nerve agents to GB-type nerve agents.

7. The means of claim 2 wherein said sheet member is wettable by said chemical agent and is adapted to cause a substantial increase in liquid surface area upon contact of a liquid droplet therewith.

8. The means of claim 7 wherein said sheet member comprises finely woven screen or fabric having openings substantially smaller than 50 microns.

9. The means of claim 7 wherein said sheet member comprises a metal fibril mat.

10. The means of claim 9 wherein said metal fibrils are stainless steel, wherein the thickness of said mat is in the range of about 0.01 to 0.02 inches and wherein the nominal pore size is about 20 microns.

11. The means of claim 2 wherein said collector assembly includes a pair of said collector means and wherein said collector assembly is disposed at a location above said detection and alarm device.

12. The means of claim 11 wherein each of said pair of collector means is pivoted along a side thereof and is movable from a generally horizontal to a generally vertical position.

13. The means of claim 2 wherein said collector means are mounted upon a bearing support and are freely rotatable about a vertical axis and wherein said sheet member is canted at an angle to the horizontal, said collector means adapted to cause said sheet member to face into the prevailing wind.

14. The means of claim 2 wherein said sheet member has a surface area in the range of 5 to 50 square inches.

15. A method for detecting falling liquid droplets of a chemical agent comprising:
intercepting said falling droplets;
causing said intercepted droplets to vaporize;
pneumatically transporting the droplet vapor in a constant volume air stream to a detector;
passing said air stream and said vapor through the detector, and
producing a signal responsive to the presence of chemical agent in said detector.

16. The method of claim 15 wherein droplets are intercepted upon a sheet member which is permeable to air and is adapted to enhance the vaporization of liquid thereon.

17. The method of claim 16 wherein said constant volume air stream is drawn through said sheet member.

18. The method of claim 17 wherein said sheet member comprises a metal fibril mat.

19. The method of claim 17 wherein said chemical agent comprises a chemical warfare agent.

20. The method of claim 17 wherein said chemical agent comprises a pesticide or herbicide.

21. A device for detecting falling liquid droplets of a chemical agent comprising:
droplet collecting means disposed to intercept falling liquid droplets, said collecting means including a sheet member permeable to air and adapted to vaporize said liquid droplets;
housing means enclosing a chamber disposed about the bottom side of said sheet member;
detector means adapted to produce a signal upon passage of chemical agent vapor therethrough;
conduit means communicating between said chamber and said detector means, and means for drawing an air stream through said collecting means, conduit means and detector.

22. The device of claim 21 wherein said sheet member has a surface area greater than about 5 square inches and is of substantially uniform porosity and permeability.

23. The device of claim 22 wherein said sheet member is wettable by said chemical agent and is adapted to cause a substantial increase in liquid surface area upon contact of a liquid droplet therewith.

24. The device of claim 23 wherein said sheet member comprises finely woven screen or fabric having openings smaller than about 50 microns.

25. The device of claim 23 wherein said sheet member comprises a metal fibril mat.

26. The device of claim 25 wherein said metal fibrils are stainless steel and wherein said mat thickness is in the range of about 0.01 to 0.02 inches.

27. The device of claim 21 wherein said detector comprises an ionization cell employing a radioactive source.

28. The device of claim 21 wherein said droplet collection means is canted at an angle to the horizontal, is mounted upon a bearing support so as to be freely rotatable about a vertical axis, and is adapted to face into the prevailing wind.

29. Means for intercepting and vaporizing falling liquid droplets of a chemical agent comprising:
collecting means having a upper surface disposed transversely across the path of said falling droplets, said collecting means comprising an air permeable member positioned at a location free from obstruction to said falling droplets and adapted to cause vaporization of said droplets upon impact;
chamber means formed about a lower surface of said collecting means, and
means to draw air through said permeable member.

30. The means of claim 29 wherein said air permeable member is wettable by said chemical agent and is adapted to cause a substantial increase in liquid surface area upon contact of a liquid droplet therewith.

* * * * *